United States Patent [19]

Hesse

[11] Patent Number: Plant 6,563

[45] Date of Patent: Jan. 24, 1989

[54] CHRYSANTHEMUM PLANT NAMED TANGELO

[75] Inventor: Peter S. Hesse, Bradenton, Fla.

[73] Assignee: Ball Pan Am Plant Co., Parrish, Fla.

[21] Appl. No.: 56,985

[22] Filed: Jun. 3, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Tangelo, characterized by its daisy type flowers which have orange bronze ray florets and lime green disc florets, relatively short ray florets, long sturdy peduncles, 8 week flower response.

1 Drawing Sheet

The present invention comprises a new and distinct cultivar of *Chrysanthemum morifolium,* Ramat., hereinafter referred to by the cultivar name Tangelo.

Tangelo is a mutation resulting from a controlled radiation program conducted in Parrish, Fla. in 1982 under the supervision of Peter S. Hesse. The purpose of the radiation program was to improve the orange color of the unnamed parent cultivar designated SP77-620K-BS. Cuttings of SP77-620K-BS were given 1000 RADS of X-ray energy in the radiation program. Tangelo was discovered and selected as one flowering plant within the production of the irradiated plants of the parent cultivar SP77-620K-BS by Peter S. Hesse in October 1982 in a controlled environment in Parrish, Fla.

The first act of asexual reproduction of Tangelo was accomplished when vegetative cuttings were taken from the initial selection in January 1983 in a controlled environment in Parrish, Fla. by a technician working under formulations established and supervised by Peter S. Hesse. Horticultural examination of selected units initiated in April 1983 has demonstrated that the combination of characteristics as herein disclosed for Tangelo are firmly fixed and are retained through successive generations of asexual reproduction.

The following traits have been repeatedly observed and are determined to be basic characteristics of Tangelo, which in combination distinguish this Chrysanthemum as a new and distinct cultivar:

1. Orange bronze, high quality daisy flowers, highlighted by a lime green disc.
2. Best suited for production as a cut flower with center bud removal.
3. Long sturdy peduncles, slightly compounded.
4. Ray florets 28–35 mm in length and 9–14 mm in width.
5. The average number of ray florets per capitulum is 38.
6. Eight (8) week flower response.
7. Diameter across capitulum is 65–75 mm.

Tangelo has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commerical practice.

Of the many commercial cultivars known to the present inventor, the most similar in comparison to Tangelo is the cultivar Bronze Niva. Reference is made to attached Chart A which compares certain characteristics of Tangelo to those same characteristics of Bronze Niva. In comparison to Bronze Niva, Tangelo has orange bronze flower color, more ray florets per capitulum, shorter ray florets, and smaller diameter capitulum.

The accompanying photographic drawing shows typical inflorescence and foliage characteristics of Tangelo. The photograph is in black and white, with one flower being colored to depict true flower color.

In the following description, color references are made to the Royal Horticultural Society Colour Chart. The color values were determined between 10:30 and 10:45 a.m. on May 15, 1987 under fluorescent light at Parrish, Fla.

CLASSIFICATION:

*Botanical.*—*Chrysanthemum morifolium,* Ramat., cv. Tangelo.

*Commercial.*—Cut daisy spray.

INFLORESCENCE

A. Capitulum:
- *Form.*—Flat.
- *Type.*—Single.
- *Diameter across face.*—65–75 mm.

B. Corolla of ray florets:
- *Color (general tonality from a distance of three meters).*—Orange-bronze.
- *Color (upper surface).*—172D.
- *Color (under surface).*—8B.

C. Corolla of disc florets:
- *Color (mature).*—Yellow.
- *Color* (immature).—Lime green, 142A.

D. Reproductive organs:
- *Androecium.*—Present in disc florets only.
- *Gynoecium.*—Present in both disc and ray florets.

PLANT

A. General appearance:
- *Height.*—1–2 meters; height may vary depending upon growing conditions, cultural practices or growth regulator application.

B. Foliage:
- *Color (upper surface).*—147A.
- *Color (under surface).*—147B.
- *Shape.*—Ovate, deeply lobed and serrated margins.

CHART A

| | TANGELO | BRONZE NIVA |
|---|---|---|
| Diameter across face of capitulum | 65–75 mm | 75–85 mm |
| Average number of ray florets per capitulum | 38 | 30 |
| Range of ray floret length | 28–35 mm | 30–40 mm |
| Range of ray | 9–14 mm | 9–14 mm |

CHART A-continued

| | TANGELO | BRONZE NIVA |
|---|---|---|
| floret width | | |

I claim:

1. A new and distinct cultivar of Chrysanthemum plant named Tangelo, as illustrated and described, and particularly characterized by its daisy type flowers which have orange bronze ray florets and lime green disc florets, relatively short ray florets, long sturdy peduncles, and its 8 week flower response.

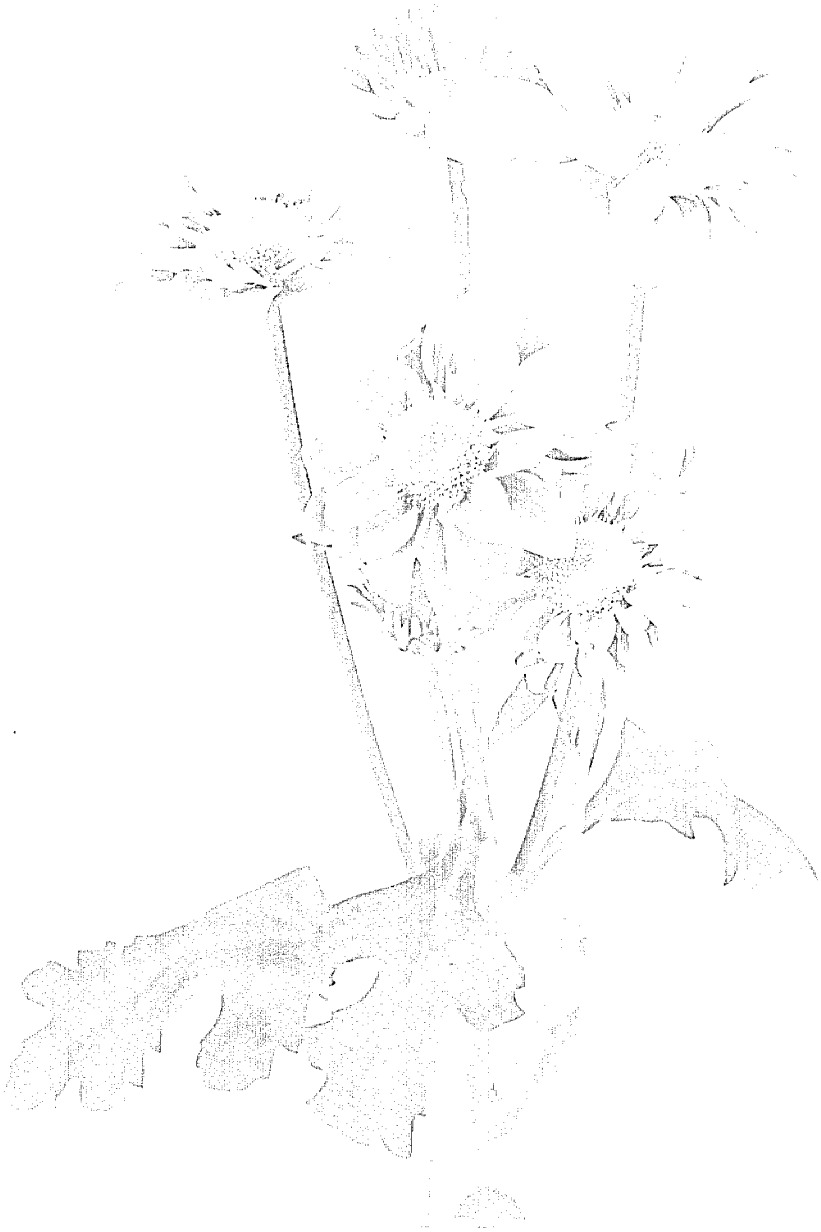

* * * * *